(12) United States Patent
Glocker et al.

(10) Patent No.: US 8,088,078 B2
(45) Date of Patent: Jan. 3, 2012

(54) METHODS AND APPARATUS FOR MEASURING PRESSURE PROFILES

(75) Inventors: Raymond Glocker, Düdingen (CH); Haldun Özdemir, Düdingen (CH)

(73) Assignee: PP-Technologies AG, Düdingen (CH)

( * ) Notice: Subject to any disclaimer, the term of this patent is extended or adjusted under 35 U.S.C. 154(b) by 117 days.

(21) Appl. No.: 10/545,175

(22) PCT Filed: Feb. 17, 2003

(86) PCT No.: PCT/CH03/00113
§ 371 (c)(1), (2), (4) Date: Nov. 22, 2005

(87) PCT Pub. No.: WO2004/071293
PCT Pub. Date: Aug. 26, 2004

(65) Prior Publication Data
US 2006/0116601 A1    Jun. 1, 2006

(51) Int. Cl.
*A61B 5/00* (2006.01)
*A61B 5/103* (2006.01)
*A61B 5/117* (2006.01)
*A61N 1/00* (2006.01)
(52) U.S. Cl. .................. 600/561; 600/593; 607/116
(58) Field of Classification Search .................. 600/561, 600/593; 607/116
See application file for complete search history.

(56) References Cited

U.S. PATENT DOCUMENTS

| 3,659,588 A | | 5/1972 | Kahn et al. |
| 4,121,159 A | * | 10/1978 | Lampert ........................ 375/358 |
| 5,062,296 A | * | 11/1991 | Migliori .......................... 73/579 |
| 5,093,723 A | * | 3/1992 | Yang .............................. 348/475 |
| 6,296,615 B1 | | 10/2001 | Brockway et al. |
| 6,450,972 B1 | * | 9/2002 | Knoll ............................. 600/561 |
| 2003/0065373 A1 | * | 4/2003 | Lovett et al. .................. 607/122 |
| 2003/0222369 A1 | * | 12/2003 | Nicora et al. ................. 264/40.5 |

FOREIGN PATENT DOCUMENTS

WO    WO 01/54563    8/2001

OTHER PUBLICATIONS

Knoll et al, "Pressure profile sensing system", Sensors and Actuators A, Elsevier Sequoia S.A., Lausanne, CH, vol. 93, No. 1, Aug. 25, 2001, pp. 52-56.

* cited by examiner

*Primary Examiner* — Max Hindenburg
*Assistant Examiner* — Sean Dougherty
(74) *Attorney, Agent, or Firm* — Nixon & Vanderhye P.C.

(57) ABSTRACT

Method and apparatus for performing multidimensional pressure measurements by means of pressure profile sensors comprises using a multichannel catheter (7), each channel (1, 2 . . . ) of which is individually excited electrically, more particularly each channel is individually and distinctly excited electrically so to provide individual, distinct excitation signals for registration. Use for performing pressure measurements in various human or animal tracts like e.g. esophagus, urethra or intestine or various cavities like e.g. stomach, bladder or uterus.

5 Claims, 2 Drawing Sheets

US 8,088,078 B2

METHODS AND APPARATUS FOR MEASURING PRESSURE PROFILES

This application is the US national phase of international application PCT/CH2003/000113 filed 17 Feb. 2003 which designated the U.S. and claims benefit of PCT/CH2003/000113, dated 17 Feb. 2003, the entire content of which is hereby incorporated by reference.

FIELD OF THE INVENTION

The invention refers to medical investigation or diagnostic tools and methods applicable to mammals, more specifically to methods for measuring pressure profiles in various body tracts or cavities.

BACKGROUND OF THE INVENTION

Among various technologies available for measuring pressures within the frame of medical investigations or diagnostic methods the Pressure Profile Sensor Method has been developed recently (PPS-Method). U.S. Pat. No. 6,459,972 of Sep. 17, 2002 and the literature cited therein provide detailed information concerning the fundamentals of that technique and its potential uses.

The basis of that highly performing technique is linked to the deformation of the shape of a saline solution caused by an external pressure when applied to the catheter lumen in which the saline solution is located; of course provided the walls of the catheter tubing in which the saline solution is filled in are thin enough to be deflected by the external pressure. As the saline solution is electrically conducting, the impedance of the saline solution will change when the shape is changed through the applied pressure along the axis of the tubing and over time, the most sensitive part of the saline solution column being the front of same. So variations of the pressure can be followed over time. As performed this method provides one-dimensional pressure profiles only.

When two- or more-dimensional pressure distribution measurements are necessary this can be performed using a plurality of tubes which are arranged in parallel, each of one being successively filled with the saline solution and then subjected to electrical excitation and eventually signal detection and integration typical of the PPS-Method referred to here above. Such a way, however, is not easy to implement in human or animal body vessels or tracts, moreover slow and complex in respect of results interpretation.

Consequently the medical community is still looking for easier and more reliable methods, especially when multi-dimensional pressure distribution in various tracts or cavities of e.g. the human body are necessary. The present invention provides a very efficient solution which easily overcomes all the obstacles currently met.

SUMMARY OF THE INVENTION

The invention provides first a method for performing pressure measurements by means of pressure profile sensors, which comprises using a multichannel catheter each channel of which being individually excited electrically.

The invention further provides using the above method for performing pressure profile measurements in body tracts or cavities such as esophagus, stomach, intestine, urinary tract, bladder or uterus.

The invention also provides a multichannel catheter useful for performing the said method which comprises an internal tubing surrounded coaxially by an external tubing and so leaving a crown inner space which is divided in two or more channels by walls which are distributed symmetrically around the longitudinal axis of the catheter.

The invention, finally, provides an apparatus suitable for performing the method defined here above, which comprises
- a single source of saline solution fitted to a single pumping tool,
- a single monitor suited to give rise to a succession of distinct excitation signals and to apply each of these excitation signals to each channel separately, and
- a single electrode applied externally to the subject for recording individually each signal from the body and transferring the individually to the recorder or analyzer tool.

BRIEF DESCRIPTION OF THE DRAWINGS

FIG. 3 more particularly shows the deformation the outer wall of a predefined lumen caused by an external pressure.

Multichannel catheters according to the invention comprise an internal tubing 5 surrounded coaxially by an external tubing 6 which set a crown spatial arrangement which is divided in two, three, four or even more lumens (channels) 1, 2 . . . by walls 3, 4, . . . distributed symmetrically around the longitudinal axis of the catheter 7.

Figure 1:
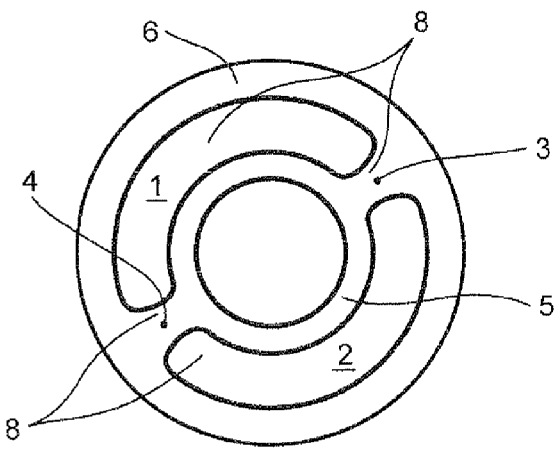
FIGS. 1, 2 and 3 illustrate specific embodiments of multichannel catheters which can be used within the frame of the present invention.
Figure 2:
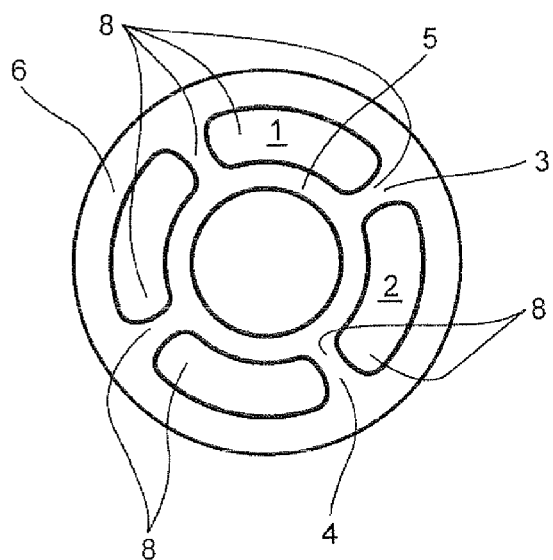
Figure 3:
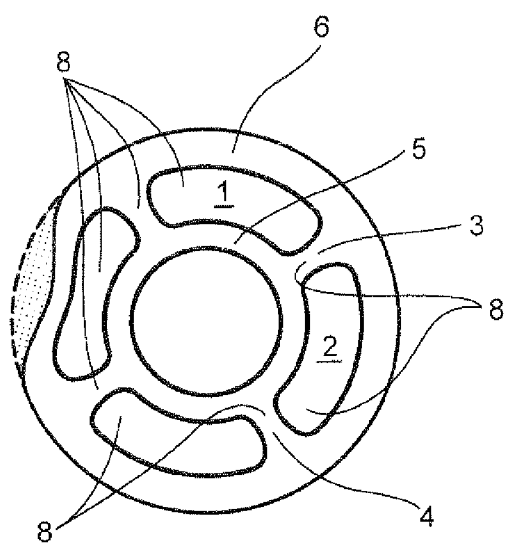
Figure 4:
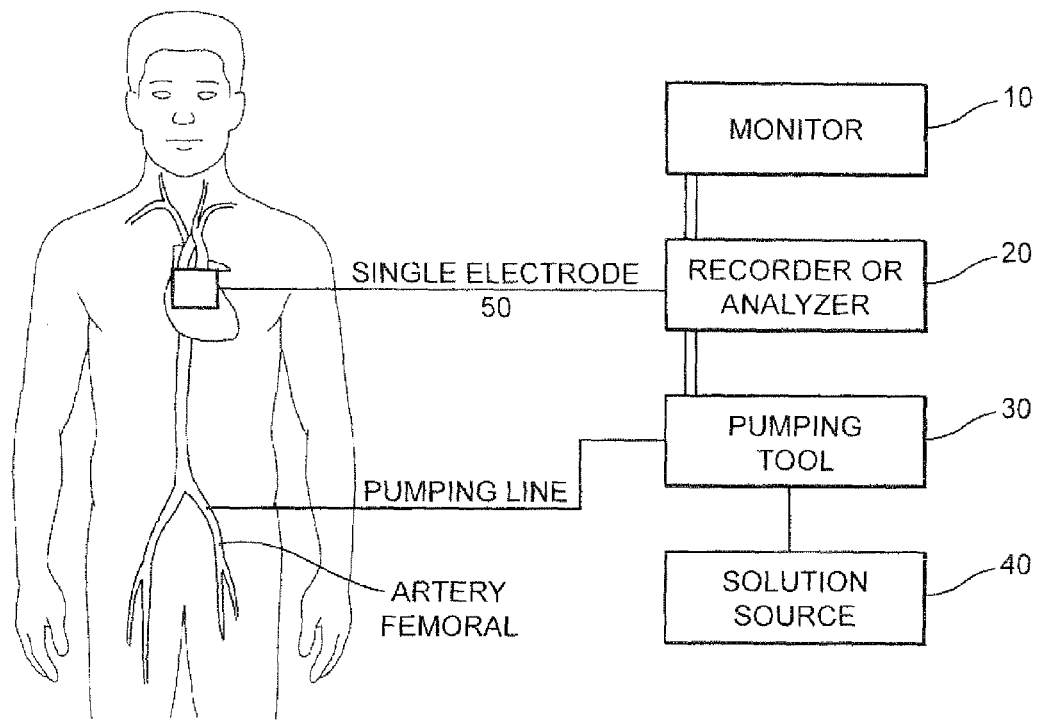
FIG. 4 illustrates a human, a monitor, a recorder or analyzer, a pumping tool, a solution source, a single electrode, and pumping line.

Accordingly, for performing the PPS measurements, and to be sure that the separated lumen will act with some detectable deformation on the corresponding external pressure originated by the corresponding space angles, the web fitted in the walls 3, 4, . . . generating the lumen 1, 2, . . . of the inner space has to be stiff enough in the said walls but soft enough in the outside tubing 6 to let the pressure deform the said outside wall 6—see FIG. 3—. A preferred configuration of a multichannel catheter is a four lumen configuration where the lumens are offset by 90 degrees—see FIG. 2.

In some embodiments the central tubing (5) can be filled with gas or liquid, or be significantly more reduce with respect to its cross section than tubing 6 or even have no interior space. It will be up to those skilled in the art to select the appropriate material and configuration depending on the specific conditions to be met.

Multichannel tubing used within the frame of the invention can be manufactured using commercially available innocuous polymer materials and techniques, e.g. extrusion forming. Suitable polymer material can be selected among silicon, rubber, latex, polyurethane, PVC, polypropylene, PE or the like. Such polymer material can further be made electrically conductive through doping with carbon or metal powder.

According to the present invention each of the lumen (channels) of catheters defined here above is electrically excited individually what affords individual signals which are eventually subject to detection, analysis, interpretation or e.g. convenient display.

Each channel is furthermore excited in such a way to provide individual, distinct excitation signals for detection and registration, i.e. channel 1 leading to a signal 1, channel 2 leading to a signal 2 distinct from signal 1, channel 3 leading a signal 3 which is distinct from both signal 1 and 2, etc. . . . . According to the invention, for predetermined excitation parameters (voltage and frequency, e.g. 2 Volts and 100 kHz respectively) the distinction of the electrical excitation applied to each individual channel can be performed by modulating either the frequency or the phase shift or both.

In that context frequency modulation can be performed by steps of at least about 0.1 kHz to about 10 kHz, e.g. 2, 5, 10 kHz preferably by steps of 1 to 10 kHz. Phase shift modulation, either performed separately from or simultaneously with frequency modulation, can be performed by steps of at least about 10 degrees, e.g. 20, 30, 90 degrees preferably by steps of 90 degrees. Simultaneous modulation of frequency and phase shift comprise preferably steps of 1 to 10 kHz and 90 degrees, respectively. Cross talk between different channels is thus avoided and then the signals are separated well enough so that they can travel individually through the body and get picked up eventually by one body electrode only and then processed according the PPS-Method.

It is of course definitely more convenient that the mechanical parts in the PPS method (stepper motor and pump head) which are used to perform the necessary saline solution oscillations shall not be duplicated, tripled or even more for a multichannel configuration. It is on the contrary more convenient to have the mechanical tools in one single configuration only, whereas the excitation signals applied to each individual channel are treated separately. This can be performed making reference to prior known techniques as, e.g. disclosed in U.S. Pat. No. 6,450,972 which constitute integral part of the specification. An apparatus suitable for achieving the desired measurement is defined, in one embodiment (see, e.g., FIG. 4 and FIGS. 1-3, including the crown inner space (8) mentioned above in the third paragraph of the Summary of the invention), by an apparatus suitable for performing the method of performing pressure measurements by means of pressure profile sensors which comprises using a multichannel catheter, each channel of which being individually excited electrically, which comprises a single source of saline solution (40) fitted to a single pumping tool (30), a single monitor (10) suited to give rise to a succession of distinct excitation signals and to apply each of these excitation signals to each channel separately, and a single electrode (50) applied externally to the subject (e.g., human) for recording individually each signal from the body and transferring the individually to the recorder or analyzer tool (20).

By means of the invention those skilled in the art will be able to perform a wide range of pressure measurements in various human or animal tracts like e.g. oesophagus, urethra or intestine, or various cavities like e.g. stomach, bladder, or uterus. The multichannel catheter technique is particularly convenient for analysing the space angle dependency of the pressure which acts on said catheter, specially when more than one lumen (channel) is squeezed when subject pressure in locations such as sphincters.

For carrying out the method with a maximized accuracy is it recommended to perform first electrical excitation of one channel only (e.g. channel 1) and to apply an outside reference pressure signal from a relevant portion or space angle of the body so to obtain a unambiguous spatial dedication of the orientation of said channel. This might prevent unexpected distortion of pressure spatial distribution under investigation as, by themselves flexible, relatively long catheters can present a different (somewhat twisted) orientation at the measurement location than that of the proximal end.

The invention claimed is:

1. An apparatus for performing pressure measurement in a human or animal tract comprising:
    a single source of saline solution fitted to a single pumping tool,
    a multichannel catheter comprising a single electrode for all channels and having at least two channels and wherein the multichannel catheter is made from a single element within which the channels are formed, each channel being configured to be filled with said saline solution and to be individually excited electrically,
    a single monitor suited to give rise to a succession of distinct electrical excitation signals and to apply each of these electrical excitation signals to each channel separately, and
    the single electrode adapted to be applied externally to a subject for recording individually each signal from the human or animal body and transferring each signal individually to a recorder or analyzer tool.

2. An apparatus according to claim 1 containing four channels wherein said channels are offset by 90 degrees.

3. An apparatus according to claim 1, the said multichannel catheter comprising an internal tubing surrounded coaxially by an external tubing leaving a crown inner space divided in several channels separated by walls, said channels being distributed symmetrically around a longitudinal axis of the catheter, said external tubing being more sensitive to external pressure than said walls and said internal tubing.

4. An apparatus according to claim 3 wherein said internal tubing is filled with a gas or a liquid.

5. An apparatus according to claim 1, 2, 3, or 4, wherein said monitor is adapted to provide distinct electrical excitation signals which can be performed by modulating either a frequency, a phase shift, or both a frequency and a phase shift.

* * * * *